United States Patent
Johannessen (10) Patent No.: US 11,929,040 B2
(45) Date of Patent: Mar. 12, 2024

(54) CIRCADIAN LIGHTING-ENABLED DISPLAY SYSTEM, METHOD, AND APPARATUS

(71) Applicant: B/E AEROSPACE, INC., Winston Salem, NC (US)

(72) Inventor: Eric Johannessen, Holbrook, NY (US)

(73) Assignee: B/E AEROSPACE, INC., Winston Salem, NC (US)

( * ) Notice: Subject to any disclaimer, the term of this patent is extended or adjusted under 35 U.S.C. 154(b) by 0 days.

(21) Appl. No.: 17/827,238

(22) Filed: May 27, 2022

(65) Prior Publication Data

US 2023/0386418 A1 Nov. 30, 2023

(51) Int. Cl.
*G09G 3/34* (2006.01)
*A61N 5/06* (2006.01)

(52) U.S. Cl.
CPC ......... *G09G 3/3413* (2013.01); *A61N 5/0618* (2013.01); *A61N 2005/0629* (2013.01); *A61N 2005/0663* (2013.01); *G09G 2300/0452* (2013.01); *G09G 2320/0666* (2013.01)

(58) Field of Classification Search
CPC ......... G09G 3/3413; G09G 2300/0452; G09G 2320/0666; A61N 5/0618; A61N 2005/0629; A61N 2005/0663
See application file for complete search history.

(56) References Cited

U.S. PATENT DOCUMENTS

| | | | |
|---|---|---|---|
| 9,039,746 B2 * | 5/2015 | van de Ven | H05B 45/00 606/88 |
| 9,844,116 B2 | 12/2017 | Soler et al. | |
| 9,913,341 B2 | 3/2018 | Maxik et al. | |
| 10,701,776 B2 | 6/2020 | Petluri et al. | |
| 11,034,451 B2 | 6/2021 | Gehle et al. | |
| 11,371,660 B2 * | 6/2022 | Petluri | H05B 45/20 |

(Continued)

FOREIGN PATENT DOCUMENTS

| | | |
|---|---|---|
| JP | 2005063687 | 3/2005 |
| WO | 2021127403 | 6/2021 |
| WO | 2021204934 | 10/2021 |

OTHER PUBLICATIONS

European Patent Office, European Search Report dated Sep. 29, 2023 in Application No. 23172572.2.

*Primary Examiner* — Kenneth B Lee, Jr.
(74) *Attorney, Agent, or Firm* — SNELL & WILMER L.L.P.

(57) ABSTRACT

A user interface display may have a display and may have a backlight that lights the display. The display may implement pixels to generate colors and images. The display may be backlit. The backlight may use pixels having emitters to generate different color backlighting. In various instances, the display or the backlight or both may include a deep blue emitter. The blue emitter may be used in combination with red and green pixels elements to generate different colors. By implementing deep blue emitters rather than conventional blue (e.g., cyan) emitters, the effects of cyan light on a viewer's circadian rhythm may be limited or eliminated. Moreover, by implementing deep blue emitters, the effects of cyan light on a viewer's circadian rhythm may be varied, while the colors and images are reproduced for viewing without introducing significant color distortion.

12 Claims, 5 Drawing Sheets

(56) References Cited

U.S. PATENT DOCUMENTS

| | | | |
|---|---|---|---|
| 2004/0156192 A1* | 8/2004 | Kerr | H05B 47/175 362/154 |
| 2014/0226110 A1* | 8/2014 | Doyle | G02F 1/133603 349/69 |
| 2015/0009242 A1 | 1/2015 | Park | |
| 2016/0121073 A1 | 5/2016 | Mok et al. | |
| 2021/0097943 A1* | 4/2021 | Wyatt | H10K 59/351 |
| 2021/0309386 A1 | 10/2021 | Johannessen | |
| 2021/0329757 A1* | 10/2021 | Peeters | F21V 9/30 |

* cited by examiner

CIRCADIAN LIGHTING-ENABLED DISPLAY SYSTEM, METHOD, AND APPARATUS

FIELD

The present disclosure relates generally to a display system, method, and apparatus and more particularly, to a circadian lighting-enabled display system, method, and apparatus.

BACKGROUND

Display systems such as electronic display monitors frequently operate by combining red, green, and cyan light sources together to generate different colors of light to display text and images. However, cyan light has been demonstrated to cause specific physiological effects on viewers. For instance, cyan light may interact with a circadian rhythm of a viewer of the electronic display monitor. Thus, there is a need for systems, methods, and apparatuses to generate different colors of light to display text and images without use or with reduced use of a cyan light sources and without causing or reducing corresponding distortions in the perceived color of the text and images.

SUMMARY

A circadian lighting-enabled display system is provided. The system may have a user interface device. The user interface device may have a device and a backlight. At least one of the display and backlight may include a pixel. The pixel may have a red emitter, a green emitter, and a deep blue emitter. The pixel may not have (may omit) a cyan emitter. In further instances, the pixel may also include the cyan emitter. The deep blue emitter may emit light corresponding to a wavelength shorter than 470 nm.

The circadian lighting-enabled display system may include a pixel controller connected to the cyan emitter and to the deep blue emitter and configured to selectably activate the cyan emitter or the deep blue emitter in concert with the red emitter and the green emitter to form colors. The pixel controller may operate to only activates one of the cyan emitter or the deep blue emitter at a same time. The pixel controller may operate to not activate both of the cyan emitter and the deep blue emitter at the same time. The pixel controller may operate to activate only one of the cyan emitter or the deep blue emitter at a same time and command the other of the cyan emitter or the deep blue emitter to be deactivated at the same time.

The pixel may be located in the display. The pixel may be located in the backlight. The pixel may be located in the backlight and the display may include a further pixel. The pixel of the backlight may include the red emitter, the green emitter and the deep blue emitter while the pixel of the display includes a further red emitter, a further green emitter and a cyan emitter. The pixel may be located in the backlight and the backlight may be a white-light backlight that combines illumination of the red emitter, the green emitter, and the deep blue emitter to generate a white light.

A circadian lighting-enabled display system is provided. The system may include a user interface device having a display and a backlight. The backlight may have a pixel including a red emitter, a green emitter, a cyan emitter and a deep blue emitter and no other emitters. A pixel controller may be configured to alternately activate the cyan emitter and the deep blue emitter in concert with the red emitter and the green emitter.

The pixel controller may activate the cyan emitter during a daytime and activates the deep blue emitter during nighttime. The display may have a further pixel consisting of a further red emitter, a further green emitter, and a further cyan emitter. The pixel of the backlight may provide backlighting to the display and the pixel of the display may reproduce a moving image. The backlight may be a white-light backlight that combines illumination of the red emitter, the green emitter, and at least one of the cyan emitter and the deep blue emitter to generate a white light.

A method is also provided. The method may be a method of a circadian-enabled display of images by a display to generate moving images and a backlight to illuminate the display. The method may include activating, by a pixel controller, the display to generate the moving images. The method may include activating, by the pixel controller, a red emitter of a pixel of the backlight to illuminate the display. The method may include activating, by the pixel controller, a green emitter of the pixel of the backlight to illuminate the display. The method may include activating, by the pixel controller, a deep blue emitter of the pixel of the backlight to illuminate the display. The blue emitter may emit light corresponding to a wavelength shorter than 470 nm.

In various embodiments, the method also includes deactivating, by the pixel controller, a cyan emitter of the pixel of the backlight. The deactivating may be to refrain from illuminating the display with the cyan emitter. The method may include deactivating, by the pixel controller, the deep blue emitter of the pixel of the backlight and activating, by the pixel controller, a cyan emitter of the pixel of the backlight, wherein a color generated by the pixel with the red emitter, the green emitter, and the cyan emitter activated and a color generated by the pixel with the red emitter, the green emitter, and the deep blue emitter activated is a same color. The color may be white. The color generated by the pixel with the red emitter, the green emitter, and the cyan emitter activated may have a different power spectral distribution than the color generated by the pixel with the red emitter, the green emitter, and the deep blue emitter.

The pixel controller may activate only one of the cyan emitter or the deep blue emitter at a same time. The pixel controller may not activate both of the cyan emitter and the deep blue emitter at the same time. The pixel controller may activate the cyan emitter during a daytime and activates the deep blue emitter during a nighttime.

The forgoing features and elements may be combined in various combinations without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the following detailed description and claims in connection with the following drawings. While the drawings illustrate various embodiments employing the principles described herein, the drawings do not limit the scope of the claims.

DETAILED DESCRIPTION

The following detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that changes may be made without departing from the scope of the disclosure. Thus, the detailed description herein is presented for purposes of illustration only and not of limitation. Furthermore, any reference to singular includes plural embodiments, and any reference to more than one component or step may include a singular embodiment or step. Also, any reference to attached, fixed, connected, or the like may include permanent, removable, temporary, partial, full or any other possible attachment option. Additionally, any reference to without contact (or similar phrases) may also include reduced contact or minimal contact. It should also be understood that unless specifically stated otherwise, references to "a," "an" or "the" may include one or more than one and that reference to an item in the singular may also include the item in the plural. Further, all ranges may include upper and lower values and all ranges and ratio limits disclosed herein may be combined.

Conventional blue light pixels or emitters are termed "cyan" light pixels or emitters herein due to the significant cyan component in their spectrum and/or blue spectrum sufficiently close to cyan to have significant melatonin suppressing effects. In contrast, reference is made throughout this document to "deep blue" pixels or emitters, which is not referring to conventional blue pixels or emitters but a deep blue pixel or emitter with a spectrum that does not have significant melatonin suppressing effects. As used herein, deep blue light may be about 430 nm to about 470 nm, or 430 nm to 470 nm, or 450 nm+/−10 nm, or a wavelength shorter than about 470, or a wavelength shorter than 470 nm. As used herein, cyan light may be about 470 nm to 520 nm, or 470 nm to 520 nm, or 495 nm+/−10 nm, or a wavelength longer than about 470 nm or a wavelength longer than 470 nm.

Generally, video displays for aerospace and other uses implement pixels with red, green, and cyan (conventional blue light) emitters. To make different colors or to make white light, the video displays combine different amplitudes of red, green, and cyan light which, in combination, appear as different colors to a viewer. It is known that cyan light wavelengths affect circadian rhythms. For instance, cyan light exposure may suppress melatonin production in humans, promoting wakefulness. This may be problematic in personal entertainment devices (PEDs). In various prior instances, this is addressed by shifting the mixture of red, green, and cyan pixel illumination toward an orange color, distorting the reproduction of colors and images and creating an unaesthetic and inaccurately reproduced image.

The system, method, and apparatus disclosed herein, in various embodiments, relate to generating images that have a more pleasing aesthetic and are accurately reproduced. The systems, methods, and apparatuses further allow the purposeful addition of high levels of cyan light to promote wakefulness or to eliminate cyan light when wakefulness is not desired to be promoted, such as during nighttime use of a PED. The mixture of cyan and other colors may be varied and may fade along a range. The systems, methods, and apparatuses, in various embodiments, maintain the same perceptual metamers along the range. A metamer is color stimuli that has different spectral radiant power distributions that are perceived as identical for a given observer. In colorimetry, metamerism is a perceived matching of colors with different (nonmatching) spectral power distributions. By mixing red, green, and cyan light in different combinations, or by mixing red, green, and deep blue light in different combinations, an identical perceived color may be generated, though one mix contains cyan light and the other contains deep blue light. Mixtures containing cyan light suppress melatonin production, while mixtures continuing deep blue light instead of cyan light cause less suppression of melatonin.

The system, method, and apparatus can be implemented in an aircraft cabin lighting system, or in display screens in an aircraft cabin (such as seatback entertainment screens in a passenger cabin of an aircraft). A night mode may be implemented that avoids light wavelengths that suppress melatonin production and hamper sleep. A day mode may be implemented that achieves full brightness and increased melanopic response (melatonin production suppression) and encourages wakefulness.

Figure 1:
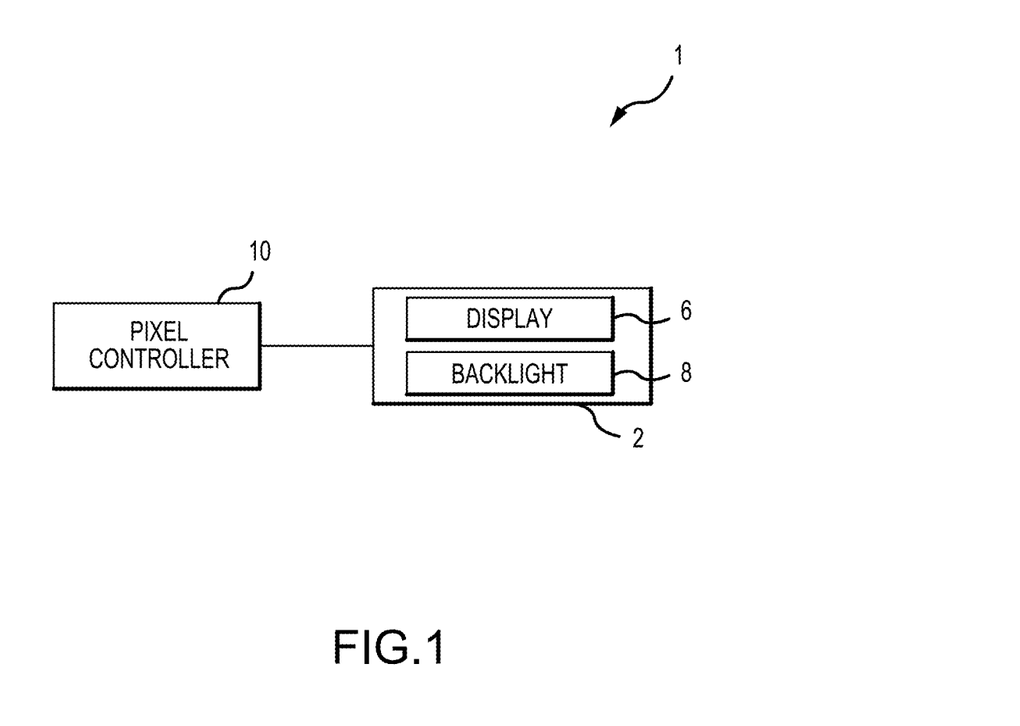
FIG. 1 illustrates a block diagram of a circadian lighting-enabled display system, in accordance with various embodiments.

Directing attention to FIG. 1, a circadian lighting-enabled display system 1 may include a user interface device 2. The user interface device 2 may comprise any device that generates visual sensory stimulation perceptible by a human. In various embodiments, the user interface device 2 may comprise an electronic visual display. For instance, the user interface device may be a seatback entertainment screen in a passenger cabin of an aircraft. The user interface device 2 may be a flight deck instrument display in a cockpit of an aircraft. In other embodiments, the user interface device 2 may be a display in a different vehicle, such as a land-based or sea-based vehicle. Finally, the user interface device 2 may be a human-machine interface device, such as a touchscreen, or a non-touch screen, or a smartphone display screen, or the like.

The circadian lighting-enabled display system 1 may include a pixel controller 10. A pixel controller 10 comprises a computer, processor, microprocessor, control circuit, or any other machine or circuit configured to selectably turn emitters of the pixels of the user interface device 2 on or off and to vary the intensity of the light passing through or emitting from the emitters. In various embodiments, the pixel controller 10 is integrated into a common housing with the user interface device 2. In further embodiments, the pixel controller 10 is separate from the user interface device 2. The pixel controller 10 may include hardware and/or software components.

The user interface device 2 may include various aspects. With ongoing attention to FIG. 1 and with additional attention to FIG. 2, a user interface device 2 may include a backlight 8. A backlight 8 may comprise light emitting diodes or may be a fluorescent backlight, or any backlight 8 as desired. The user interface device 2 may also include a display 6. The display 6 may comprise a flat-panel display device generating text, graphics, and/or moving images for visual perception by a user. Finally, the user interface device 2 may include a filter 4. A filter 4 may comprise a light-transmissive panel adjacent to the display 6 and configured to reduce transmission of one or more wavelength of light from the user interface device 2 (e.g., from the backlight 8, the display 6, and/or the combination of the backlight 8 and the display 6) to a user for visual perception. In various embodiments, the filter 4 may have multiple passbands of different center frequencies and of different (or same) bandwidths.

Figure 3:
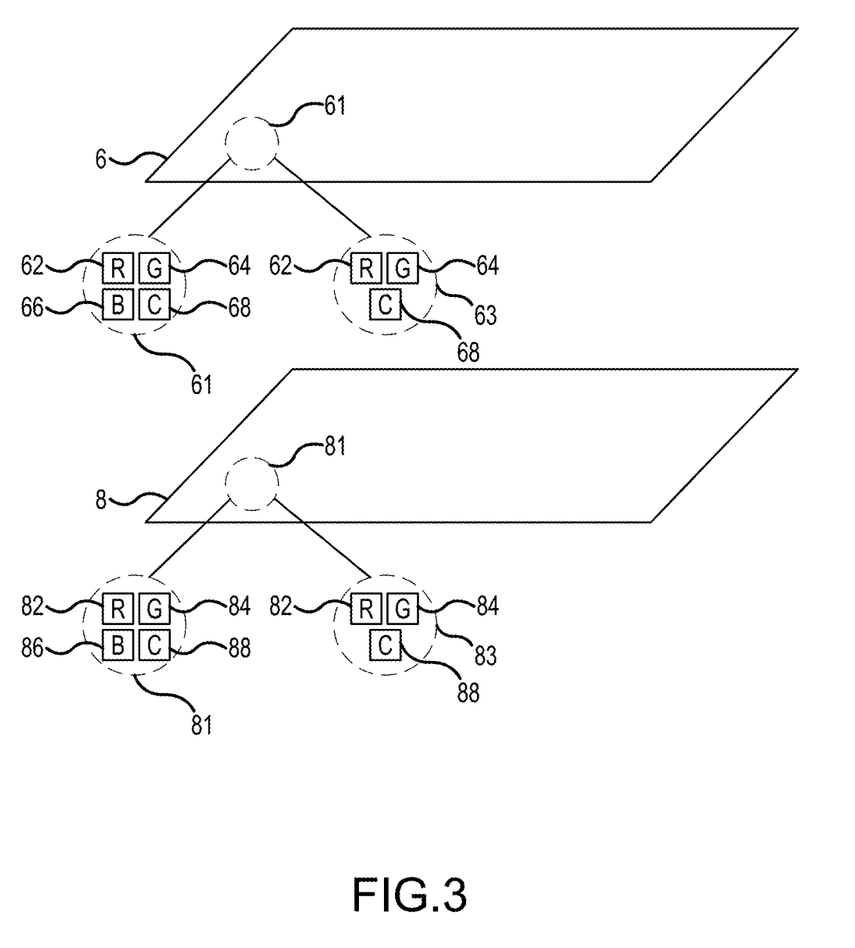
FIG. 3 illustrates multiple example configurations of pixels of a display and of a backlight of a user interface device, in accordance with various embodiments.

Turning attention to FIG. 3, various different configurations of a display 6 and a backlight 8 are depicted. For ease of discussion, these different configurations are shown in a single figure, though one may appreciate that in a practical embodiment, the different configurations may be implemented in different displays or backlights, rather than in a same display and in a same backlight as shown in FIG. 3.

A backlight 8 may have a plurality of pixels. The pixels may be made up of emitters. The emitters may be light emitters, such as light emitting diodes to generate illumination that lights a display 6. In various instances, collections of emitters comprising differently colored light emitters may be clustered as single pixels having variable color. For instance, a red light emitter, a green light emitter, and a cyan light emitter may be clustered as a single pixel capable of generating light of any color. Similarly, a red light emitter, a green light emitter, and a deep blue light emitter may be clustered as a single pixel capable of generating light of any color. In yet further instances, a red light emitter, a green light emitter, a cyan light emitter, and a deep blue light emitter may be clustered as a single pixel capable of generating light of any color and generating those colors so that identical metamers have different spectral power distributions. The light emitters may be light emitting diodes (LEDs) or may be organic light-emitting diode (OLED) devices or may be organic electroluminescent (organic EL) diodes, or may be quantum dots, such as photo-emissive quantum dots. Thus, one may appreciate that a pixel may generate a color in such a manner as to suppress melatonin and may also generate the same color in such a manner as to not suppress melatonin in a viewer.

A display 6 may have a plurality of pixels. The pixels may have one or more emitter. The emitters may be liquid crystal elements. The liquid crystal elements may selectively pass or block illumination from the backlight 8. The emitters may selectively pass or block illumination from the backlight 8 according to different colors of the backlight. In further instances, the backlight produces a white light and the emitters selectively pass or block different wavelengths of light to generate colors. In yet further instances, the display 6 may be provided without a backlight and may be light emitting. For instance, the display 6 may be provided without a backlight and may be an diode display or may be a quantum display, such as a photo-emissive quantum dot display. The display 6 may have an emissive electroluminescent layer that emits light. In various instances, emitters may emit different color light. While pixels are shown as a cluster of emitters that are light emitting elements emitting different colors, one may appreciate that a practical display 6 may operate according to various other principles, such as having a cluster of emitters that selectively pass or block light of different colors.

Thus, the display 6 may have different light emitting or light blocking elements, which may be color specific, termed herein as emitters of a pixel. A display 6 may have pixels with a red emitter, a green emitter, and a cyan emitter clustered as a single pixel capable of generating light of different colors. A display 6 may have pixels with a red emitter, a green emitter, and a cyan emitter clustered as a single pixel capable of passing light generated by a backlight 8 of different colors. A display 6 may have pixels with a color-agnostic element that operates to pass or block light from a backlight 8.

A display 6 may have pixels with a red emitter, a green emitter, and a deep blue emitter clustered as a single pixel capable of generating light of different colors. A display 6 may have pixels with a red emitter, a green emitter, and a deep blue emitter clustered as a single pixel capable of passing light generated by a backlight 8 of different colors.

A display 6 may have pixels with a red emitter, a green emitter, a cyan emitter, and a deep blue emitter clustered as a single pixel capable of generating light of different colors. A display 6 may have pixels with a red emitter, a green emitter, a cyan emitter, and a deep blue emitter clustered as a single pixel capable of passing light generated by a backlight 8 of different colors.

These different configurations are illustrated in FIG. 3. FIG. 3 shows a display 6 with a red emitter 62, a green emitter 64, a cyan emitter 66 and a deep blue emitter 68 making up a pixel 61. Alternatively, FIG. 3 shows a display 6 with a red emitter 62, a green emitter 64, and a deep blue emitter 68 making up a pixel 63. FIG. 3 also shows a backlight 8 with a red emitter 82, a green emitter 84, a cyan emitter 86 and a deep blue emitter 88 making up a pixel 81. Alternatively, FIG. 3 shows a backlight 8 with a red emitter 82, a green emitter 84, and a deep blue emitter 88 making up a pixel 83. Different combinations of pixels 61, 63, 81, and 81 may be implemented in a practical embodiment.

Figure 2:
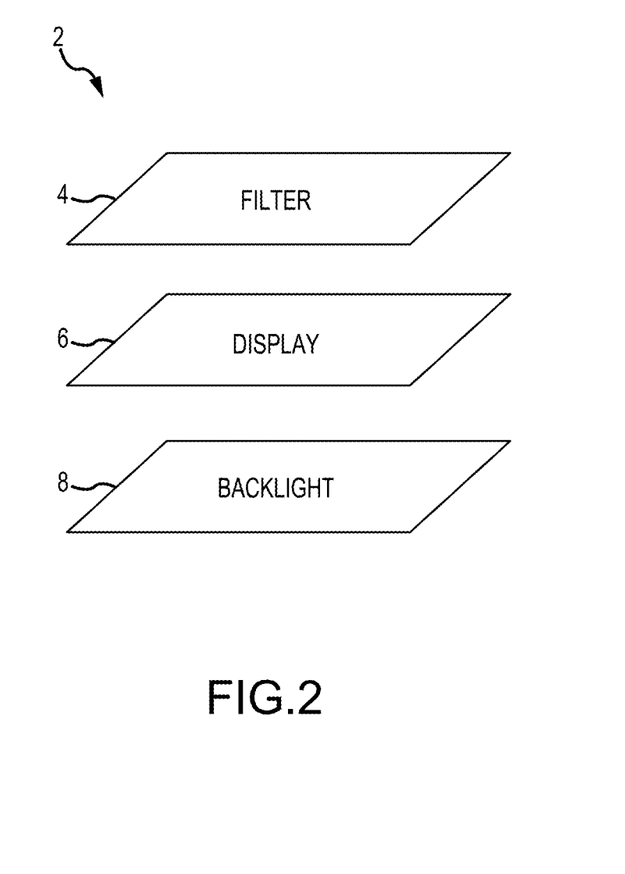
FIG. 2 illustrates a block diagram of aspects of a user interface device of the circadian lighting-enabled display system, in accordance with various embodiments.

With combined reference to FIGS. 1, 2 and 3, a circadian lighting-enabled display system may include various of the features recited operating in various configurations. One example arrangement of features is discussed below.

An example circadian lighting-enabled display system 1 has a user interface device 2 with a display 6 and a backlight 4. One or both of the display 6 and backlight 4 may have a plurality of pixels (pixel 61, 68, 81, or 83). As shown in FIG. 3, various configurations are possible for each pixel of the plurality of pixels. For instance, the pixel may have a red emitter, a green emitter and a deep blue emitter, however, in some instances a cyan emitter is also present. In other instances, the pixel does not include a cyan emitter.

A pixel controller 10 is connected to the user interface device 2. The pixel controller 10 connects to the emitters of the pixels of the user interface device 2. For example, the pixel controller 10 connects to the cyan emitter and the deep blue emitter and operates to turn them on and off or change the amplitude of light passed through or emitted by the emitters. A backlight 8 may have a pixel 81 with a red emitter 82, a green emitter 84, a cyan emitter 86, and a deep blue emitter 88. The pixel controller 10 may selectably activate the cyan emitter 86 or the deep blue emitter 88 in concert with the red emitter 82 and the green emitter 84 to form colors.

A pixel controller 10 may sometimes activate only one of the cyan emitter or the deep blue emitter at a same time and may not activate both of the cyan emitter and the deep blue emitter at the same time. This facilitates shifting of the power spectra density of the light without shifting the metamer of the perceived light. In some instances, the backlight 6 is a white-light backlight that combines illumination of the emitters to generate a white light. The generated white light may have an apparent white color when perceived by a viewer but may have different power spectral densities depending on whether the deep blue emitter or the cyan emitter is illuminated.

In some instances, a backlight 8 includes a pixel having emitters and a display 6 also includes a pixel having emitters. For instance, the backlight 8 may have a backlight pixel 81, 83 with backlight emitters and the display 6 may have a display pixel 61, 68 with display emitters. The backlight 8 emitters may be a red emitter 82, a green emitter 84, and a deep blue emitter 88 and the display emitters may be a red emitter 62 a green emitter 64, and a cyan emitter 66. Other combinations are also possible.

Continuing reference to FIGS. 1-3, another example configuration may include a circadian lighting-enabled display system 2 with a user interface device 4 that has a display 6 and a backlight 8. The backlight 8 has pixels 81. A pixel 81 may consist of a red emitter 82, a green emitter 84, a cyan emitter 86 and a deep blue emitter 88 and no other emitters. The pixel controller 10 connected to the user interface device 4 alternately activates the cyan emitter 86 and the deep blue emitter 88, in concert with the red emitter 82 and the green emitter 84. For instance, the pixel controller 10 may activate the cyan emitter 86 during a daytime and may activate the deep blue emitter 88 during a nighttime. The display 6 may have a further set of pixels 61 that also include emitters 61. The display pixels 61 may be light emitting, or may be light transmissive, meaning they do not emit light but operate to transmit or suppress light of the backlight. The display may have a pixel 61 consisting of a red emitter 62, a green emitter 64, and a cyan emitter 66, but omitting a deep blue emitter 68 and not including any other emitters. The display may have a pixel 61 consisting of a red emitter 62, a green emitter 64, and a deep blue emitter 68, but omitting a cyan emitter 66 and not including any other emitters. The backlight pixels of the backlight 8 may provide backlighting to the display 6, while the display pixels of the display 6 reproduce moving images for viewing by a user. The backlight 6 may be a white-light backlight that combines illumination of the emitters of the pixel 81 to generate a white light. The backlight 6 may be controlled by the pixel controller 10 to alternately generate white light with greater or lesser melatonin suppressing effect by changing the composition of the white light to include a cyan component or a deep blue component.

Figure 4:
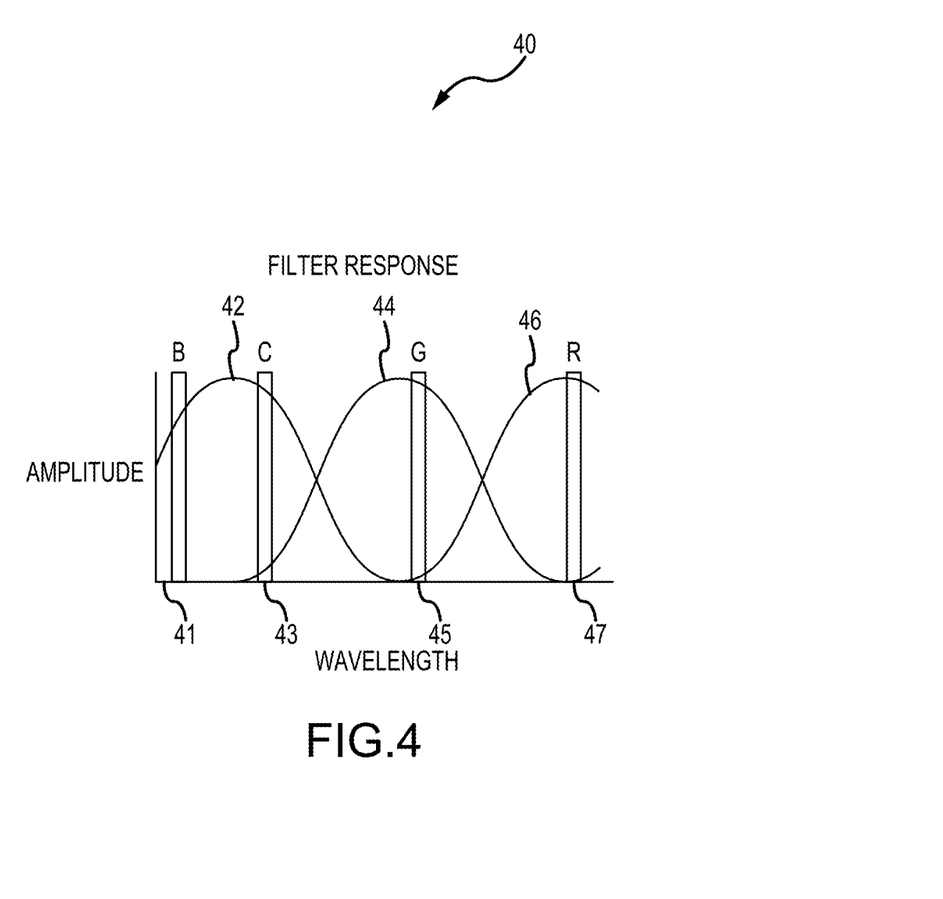
FIG. 4 illustrates an example response curve of a filter of a user interface device, in accordance with various embodiments.

With attention to FIG. 4, filter response 40 graph is illustrated showing frequency response curves associated with the filter 4 (FIG. 2). For example, the filter 4 (FIG. 2) may have various passbands for different wavelengths of light. Notably the cyan passband associated with a cyan passband response curve 42 overlaps with both the cyan light spectra 41 emitted by a cyan emitter, and also the deep blue light spectra 43 emitted by a deep blue emitter. A filter 4 (FIG. 2) can be characterized such that a pixel controller 10 adjusts the intensities of the cyan light and the deep blue light so that different spectral compositions create same metamers, allowing viewers to perceive an accurate color and brightness representation of text and images being generated by the user interface device 2 (FIG. 2). Similarly, the filter 4 (FIG. 2) may have a green passband associated with a green passband response curve 44. The green passband response curve 44 overlaps the green light spectra 45 emitted by a green emitter. The filter 4 (FIG. 2) may have a red passband associated with a red passband response curve 46. The red passband response curve 46 overlaps the red light spectra 47 emitted by the red emitter.

Figure 5:
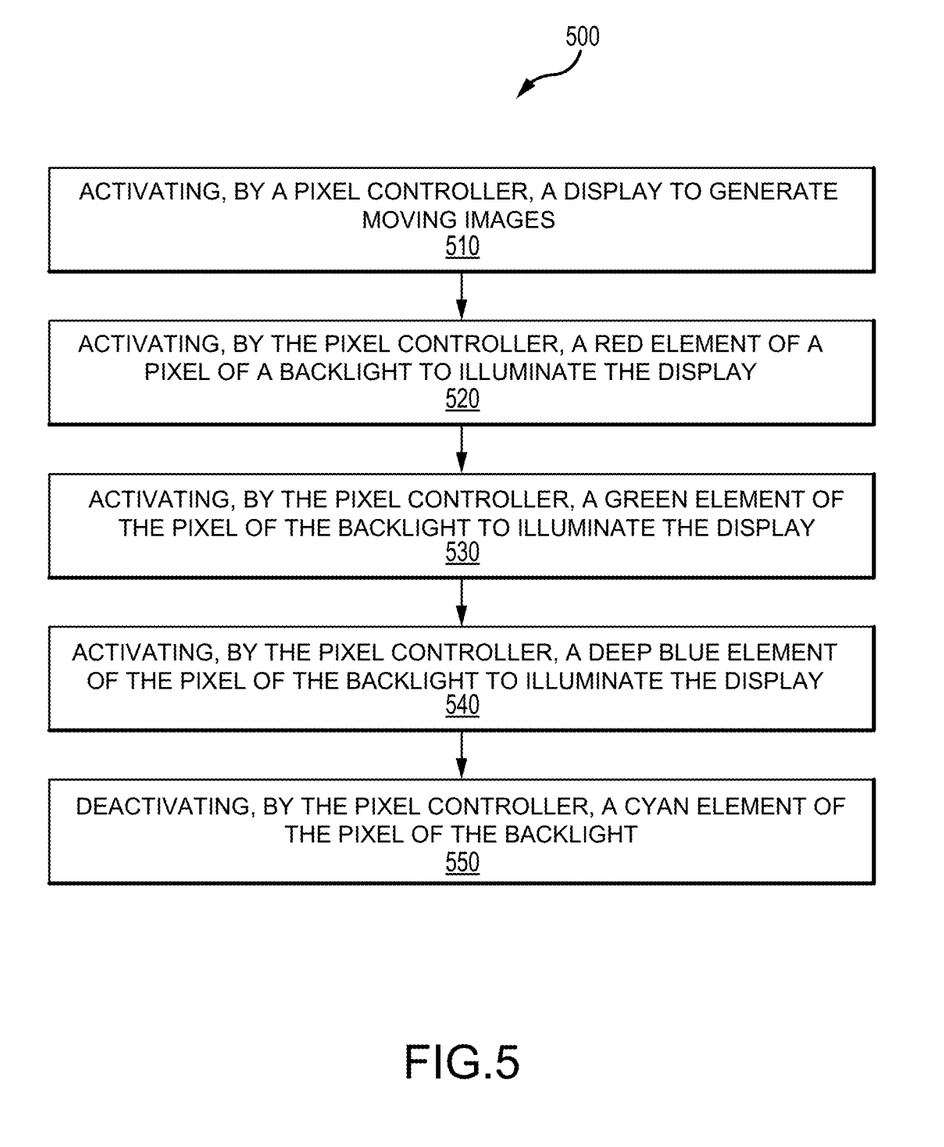
FIG. 5 illustrates a method of circadian-enabled display of images by a display to generate moving images and a backlight to illuminate the display, in accordance with various embodiments.

Finally, directing attention to FIG. 5, a method of a circadian-enabled display of images 500 is provided. The images may be displayed by a display to generate moving images. A backlight may illuminate the display. The method may include activating, by a pixel controller, the display to generate the moving images (block 510). The method may include activating, by the pixel controller, a red element of a pixel of the backlight to illuminate the display (block 520). The method may include activating, by the pixel controller, a green emitter of the pixel of the backlight to illuminate the display (block 530). The method may include activating, by the pixel controller, a deep blue emitter of the pixel of the backlight to illuminate the display (block 540).

In various embodiments, the method also includes deactivating, by the pixel controller, a cyan emitter of the backlight (block 550). Thus, the pixel controller may refrain from illuminating the display with the cyan emitter. A color generated by the pixel with the red emitter, the green emitter, and the cyan emitter activated and a color generated by the pixel with the red emitter, the green emitter, and the deep blue emitter activated is a same color. For example, the same color may be white.

In some instances, the pixel controller only activates one of the cyan pixel or the deep blue pixel at a same time. The pixel controller may deactivate the other of the cyan pixel and the deep blue pixel so that it does not activate both of the cyan pixel and the deep blue pixel at the same time. In this manner, the user interface device may switch between a mode that suppresses melatonin and a mode that does not suppress melatonin. For instance, the pixel controller may activate the cyan pixel during a daytime or other period during which melatonin suppression is favored and may activate the deep blue pixel during a nighttime or other period during which melatonin suppression is disfavored. By switching between cyan and deep blue, a same perceived color may be generated while reducing or eliminating an amount of power emitted in a portion of the light spectrum associated with melatonin suppression.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods, and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Finally, it should be understood that any of the above described concepts can be used alone or in combination with any or all of the other above described concepts. Although various embodiments have been disclosed and described, one of ordinary skill in this art would recognize that certain modifications would come within the scope of this disclosure. Accordingly, the description is not intended to be exhaustive or to limit the principles described or illustrated herein to any precise form. Many modifications and variations are possible in light of the above teaching.

What is claimed is:

1. A circadian lighting-enabled display system comprising:
   a user interface device having a display and a backlight;
   the backlight comprising a first pixel;
   the display comprising a second pixel;
   the first pixel including a first red emitter, a first green emitter, and a deep blue emitter, wherein a deep blue emitter emitting light from the deep blue emitter corresponding to a wavelength shorter than 470 nm and wherein the second pixel of the display includes a second red emitter, a second green emitter, and a cyan emitter; and
   a pixel controller connected to the cyan emitter and to the deep blue emitter and configured to either:
      activate the cyan emitter of the second pixel of the display and, responsive to activating the cyan emitter of the second pixel of the display, deactivate the deep blue emitter of the first pixel of the backlight in concert with the first red emitter, the first green emitter, the second red emitter, and the second green emitter; or
      activate the deep blue emitter of the first pixel of the backlight and, responsive to activating deep blue emitter of the first pixel of the backlight, deactivate the cyan emitter of the second pixel of the display in concert with the first red emitter, the first green emitter, the second red emitter, and the second green emitter.

2. The circadian lighting-enabled display system of claim 1, wherein
   the backlight is a white-light backlight that combines illumination of the first red emitter, the first green emitter, and the deep blue emitter to generate a white light.

3. A circadian lighting-enabled display system comprising:
   a user interface device having a display and a backlight;
   the backlight having a first pixel consisting of a first red emitter, a first green emitter, and a deep blue emitter;
   the display having a second pixel consisting of a second red emitter, a second green emitter, and a cyan emitter; and
   a pixel controller configured to either:
      activate the cyan emitter of the second pixel of the display and, responsive to activating the cyan emitter of the second pixel of the display, deactivate the deep blue emitter of the first pixel of the backlight in concert with the first red emitter, the first green emitter, the second red emitter, and the second green emitter; or
      activate the deep blue emitter of the first pixel of the backlight and, responsive to activating deep blue emitter of the first pixel of the backlight, deactivate the cyan emitter of the second pixel of the display in concert with the first red emitter, the first green emitter, the second red emitter, and the second green emitter.

4. The circadian lighting-enabled display system of claim 3, wherein the pixel controller activates the cyan emitter during a daytime and activates the deep blue emitter during a nighttime.

5. The circadian lighting-enabled display system of claim 3, wherein the pixel of the backlight provides backlighting to the display and wherein the second pixel of the display reproduces moving images.

6. The circadian lighting-enabled display system of claim 3, wherein the backlight comprises a white-light backlight that combines illumination of the first red emitter, the first green emitter, and the deep blue emitter to generate a white light.

7. A method of a circadian-enabled display of images by a display to generate moving images and a backlight to illuminate the display, the method comprising:
   activating, by a pixel controller, the backlight to generate the moving images on the display;
   activating, by the pixel controller, a first red emitter of a first pixel of the backlight to illuminate the display;
   activating, by the pixel controller, a first green emitter of the first pixel of the backlight to illuminate the display;
   activating, by the pixel controller, a deep blue emitter of the first pixel of the backlight to illuminate the display, a deep blue emitter emitting light of the deep blue emitter corresponding to a wavelength shorter than 470 nm;
   activating, by the pixel controller, a second red emitter of a second pixel of the display;
   activating, by the pixel controller, a second green emitter of the second pixel of the display;
   activating, by the pixel controller, a cyan emitter of the second pixel of the display; and
   responsive to activating the cyan emitter of the second pixel of the display, deactivating, by the pixel controller, the deep blue emitter of the first pixel of the backlight.

8. The method according to claim 7, further comprising:
responsive to reactivating the deep blue emitter of the first pixel of the backlight, deactivating, by the pixel controller, the cyan emitter of the second pixel of the display.

9. The method according to claim 8, wherein a color generated by the first pixel with the first red emitter and the first green emitter or the second red emitter and the second green emitter along with the cyan emitter activated and the color generated by the first pixel with the first red emitter and the first green emitter or the second red emitter and the second green emitter along with the deep blue emitter activated is a same color.

10. The method according to claim 9, wherein the color generated by the first pixel with the first red emitter and the first green emitter or the second red emitter and second further green emitter along with the cyan emitter activated has a different power spectral distribution than the color generated by the first pixel with the first red emitter and the first green emitter or the second red emitter and the second green emitter along with the deep blue emitter.

11. The method according to claim 9, wherein the pixel controller activates only one of the cyan emitter or the deep blue emitter at a same time.

12. The method according to claim 10, wherein the pixel controller activates the cyan emitter during a daytime and activates the deep blue emitter during a nighttime.

* * * * *